United States Patent [19]
Ozaki et al.

[11] Patent Number: 5,754,289
[45] Date of Patent: May 19, 1998

[54] RAMAN SCATTERED LIGHT MEASURING APPARATUS

[75] Inventors: Yukihiro Ozaki, Nishinomiya; Xiaoming Dou, Kyoto; Yoshinori Yamaguchi, Kyoto; Harumi Uenoyama, Kyoto, all of Japan

[73] Assignee: Kyoto Dai-ichi Kagaku Co., Ltd., Kyoto, Japan

[21] Appl. No.: 777,282

[22] Filed: Dec. 27, 1996

[30] Foreign Application Priority Data

Dec. 30, 1995 [JP] Japan .................... 7-353351

[51] Int. Cl.$^6$ ............... G01J 3/44; G01N 21/65
[52] U.S. Cl. .................... 356/301; 250/339.12
[58] Field of Search ............ 356/301; 250/339.12, 250/339.07

[56] References Cited

U.S. PATENT DOCUMENTS

| | | | |
|---|---|---|---|
| 4,648,714 | 3/1987 | Benner et al. | 356/301 |
| 4,919,533 | 4/1990 | Bowley et al. | 356/301 |
| 4,953,976 | 9/1990 | Adler-Golden et al. | 356/301 |
| 5,373,358 | 12/1994 | Adachi | 356/301 |
| 5,386,295 | 1/1995 | Switalski et al. | 356/301 |
| 5,481,113 | 1/1996 | Dou et al. | 356/301 |

FOREIGN PATENT DOCUMENTS

| | | |
|---|---|---|
| 222836 | 8/1990 | United Kingdom . |
| WO 91/11703 | 8/1991 | WIPO . |

OTHER PUBLICATIONS

"Near–Infrared Raman Spectroscopy with a 783–nm Diode Laser and CCD Array Detector," 1369 Applied Spectroscopy 43 (1989) Jan., No. 1, Frederick, MD, James M. Williamson et al.

"Frequency/Wavelength Calibration of Multipurpose Multichannel Raman Spectrometers. Part I: Instrumental Factors Affecting Precision," 1369 Applied Spectroscopy 49 (1995) Nov., No. 11, Frederick, MD, David A. Carter et al.

Primary Examiner—F. L. Evans
Attorney, Agent, or Firm—Nikaido, Marmelstein, Murray & Oram LLP

[57] ABSTRACT

A Raman scattered light measuring apparatus comprises a near infrared semiconductor laser diode as a light source for irradiating a sample with excitation light, while a photoreceiving part for receiving Raman scattered light from the sample comprises a bandpass filter having a vibration wavenumber which is specific to a sample component to be measured as a central wavelength of its transmission region, and a detector consisting of a photodiode of Ge, InAs or InGaAs or a photomultiplier having sensitivity in a near infrared region for detecting Raman scattered light which is transmitted through the bandpass filter.

7 Claims, 16 Drawing Sheets

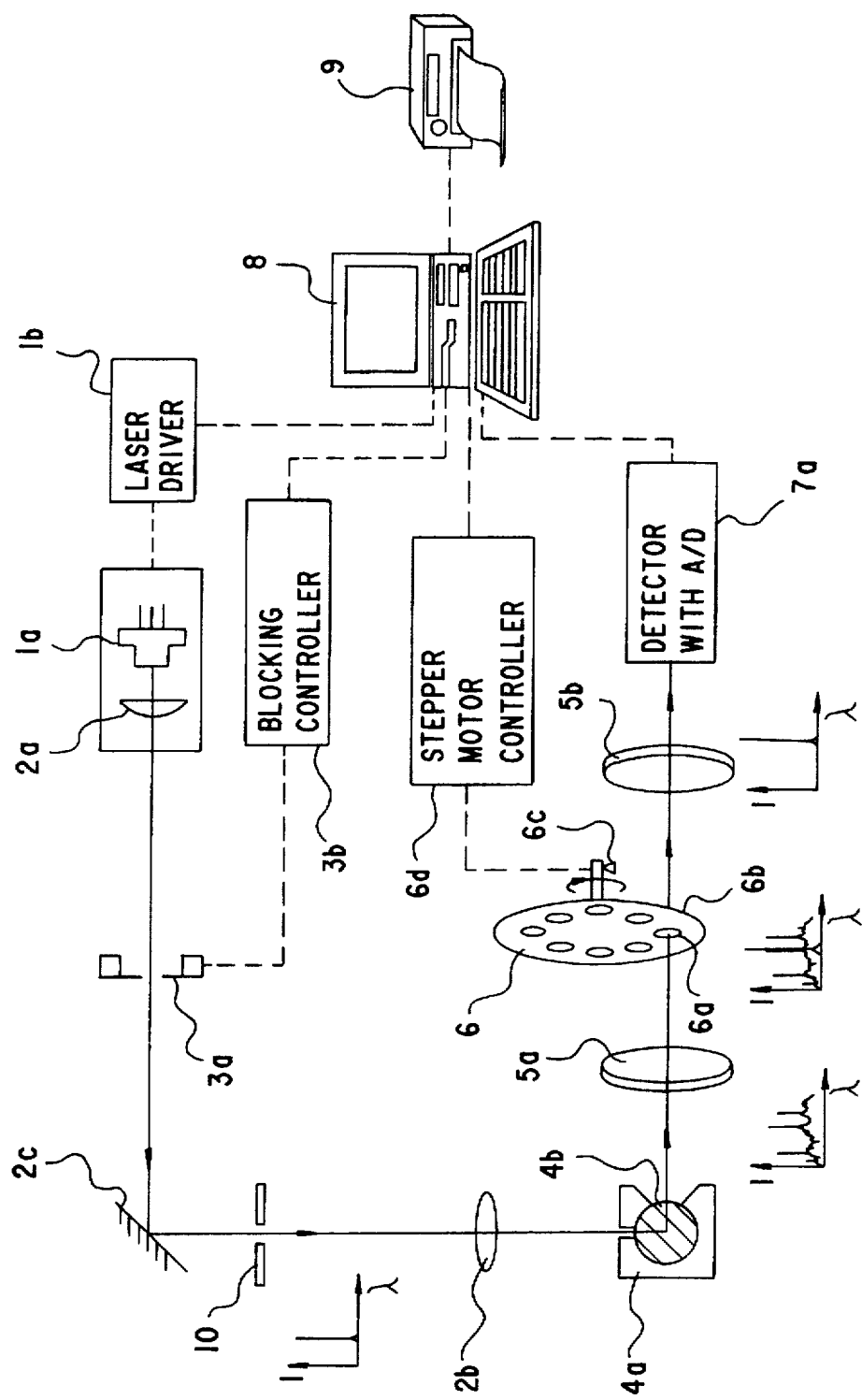

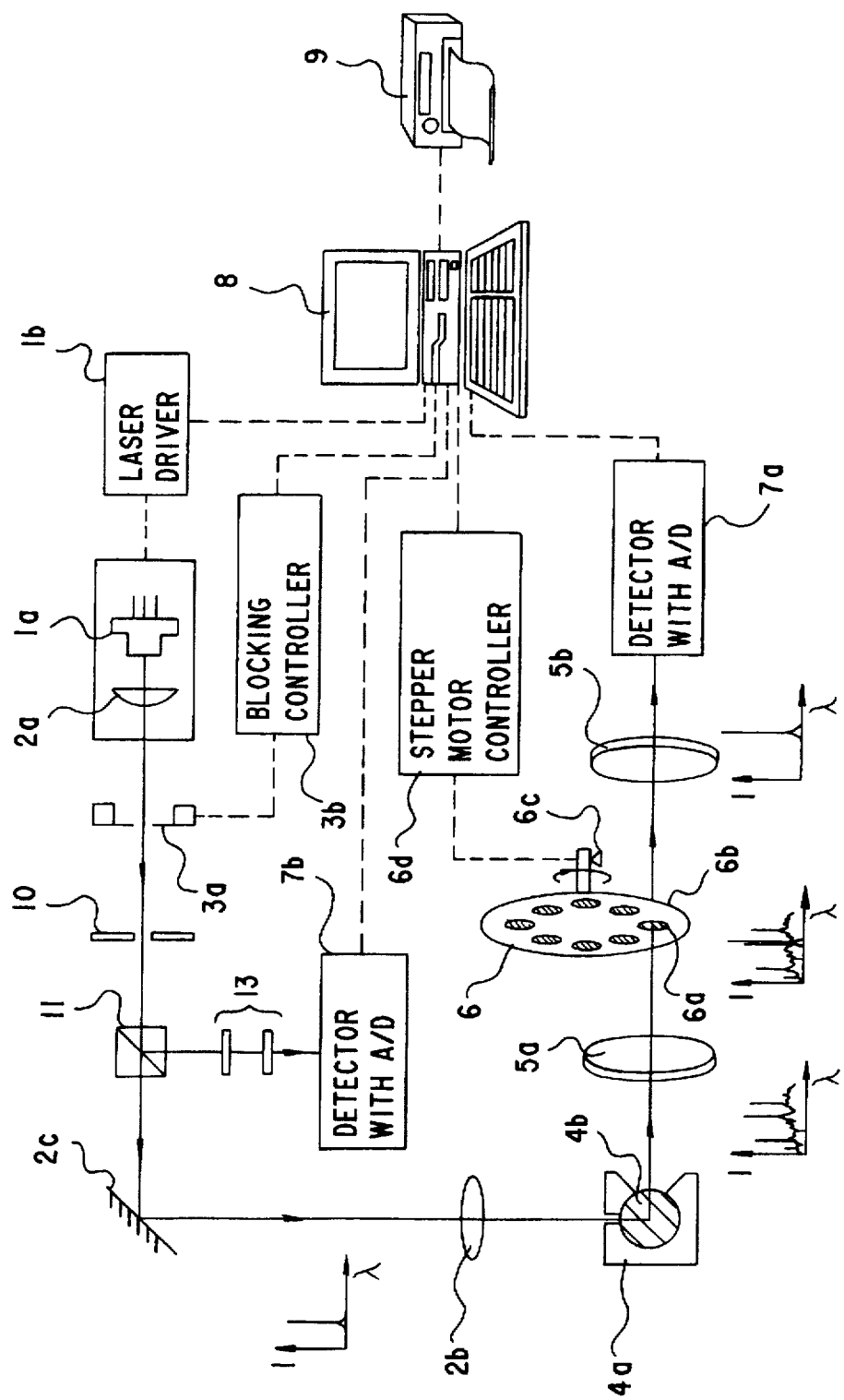

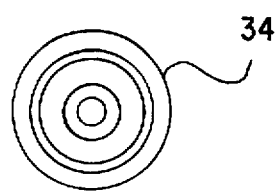
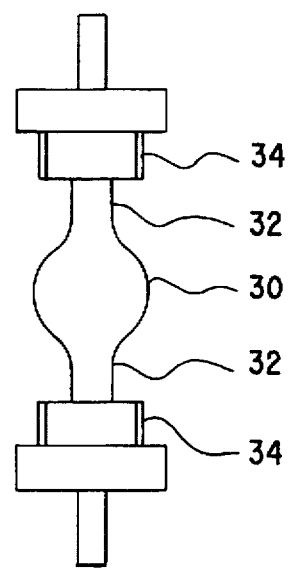
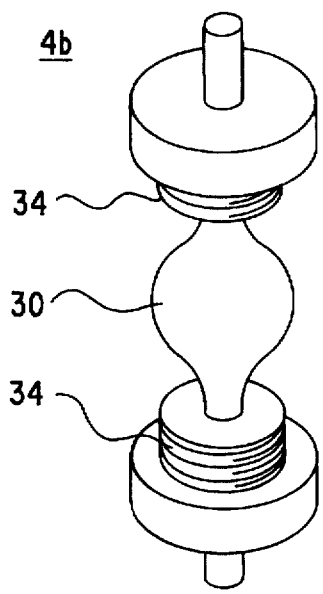

RAMAN SCATTERED LIGHT MEASURING APPARATUS

BACKGROUND OF THE INVENTION

1. Field of the Invention

The present invention relates to a scattered light measuring apparatus, and more particularly, it relates to a Raman scattered light measuring apparatus which is suitably applied to measurement of a minor component.

2. Description of the Background Art

Optical analyzing methods include Raman scattering analysis utilizing such a phenomenon that small parts of specific molecules holding photons which are irradiated with radiant energy in the form of electromagnetic radiation do not return to original vibration levels but fall to vibration levels of different electron ground states after releasing the held photons. Therefore, energy which is emitted from these molecules is specific thereto, and hence the specific molecules can be identified and determined by detecting the emitted energy as electromagnetic radiation.

While light energy emitted by Raman scattering may be in a lower energy state (Stokes Raman scattering) or a higher energy state (anti-Stokes Raman scattering) than absorbed energy, the number of electrons which are in excited states is by far smaller than the number of those in ground states, and hence anti-Stokes Raman scattering intensity is extremely weak. Therefore, measurement by Stokes Raman scattering is generally performed in a method of identifying specific molecules.

A Raman scattering spectrometric apparatus is adapted to irradiate a sample in a sample Part with excitation light from a light source part for separating Raman scattered light from the sample into its spectral components and detecting the same by a photoreceiving part, thereby measuring the concentration of a target component in the sample. Some Raman scattering spectrometric apparatuses have been proposed.

An exemplary Raman scattering spectrometric apparatus is adapted to separate Raman scattered light into its spectral components for thereafter detecting the same by a CCD detector (refer to Japanese Patent Laying-Open Gazettes Nos. 6-3271 (1994) and 5-26728 (1993)).

Another exemplary Raman scattering spectrometric apparatus is adapted to separate Raman scattered light into its spectral components for thereafter detecting the same by a photomultiplier (refer to Japanese Patent Publication No. 7-85057 (b 1995) and Japanese Patent Laying-Open Gazette No. 6-3271 (1994)).

A conventional measuring apparatus detects Raman scattered light from a sample after separating the same into its spectral components. Therefore, a spectroscope must indispensably be employed as an optical element. While spectroscopes include monodisperse, multidisperse and scanning type ones, the apparatus is increased in size and cost whatever spectroscope is employed. Further, the spectroscope is inferior in wavelength accuracy, as understood from the fact that a read wavelength with respect to a spectral wavelength must be calibrated. In addition, the measuring speed is retarded when the scanning type spectroscope is employed.

Due to the employment of the spectroscope, it is necessary to use a filter for removing Rayleigh scattered light. Due to reduction of the light quantity by the Rayleigh light removing filter and restriction of brightness and removal of stray light by the spectroscope, the light quantity of the Raman scattered light is also reduced to disadvantageously deteriorate sensitivity.

The wavelength region of an excitation light source which is generally employed in a Raman scattering spectrometric apparatus is in the range of visible to near infrared regions of 380 to 800 nm in wavelength. Considering measurement of a vital substance, the sample is easily damaged in a shorter wavelength region than 800 nm due to high photon energy. Further, a vital sample generally emits fluorescence, which is in the wavelength range of 650 to 800 nm. This wavelength range is substantially identical to a Raman shift wavelength range in case of making excitation with excitation light of a shorter wavelength region. When excitation is made with such excitation light of a shorter wavelength region, further, quantum efficiency of fluorescence generation is increased to disadvantageously hide a Raman scattering signal of the vital sample. Fluorescence is hardly generated in case of a long excitation wavelength of at least 1 μm. The quantum efficiency of Raman scattered light generation is increased as the wavelength of the excitation light is increased. In order to make Raman measurement with an excellent signal-to-noise ratio, therefore, the conventional excitation wavelength region cannot be regarded as suitable for a vital sample, but the excitation wavelength is preferably at least 800 nm in the range of 800 to 1600 nm, for example, in relation to the vital sample.

Considering that Stokes Raman scattered light is generally detected as Raman scattered light and the wavelength of such Stokes Raman scattered light is in a longer wavelength range than the excitation wavelength, sensitivity in detection of the Raman scattered light comes into question in case of employing an excitation wavelength of such a longer wavelength range. In a silicon photoreceptor or the photomultiplier employed in the citation, for example, stability and reproducibility of detection are deteriorated and dispersion type spectrometry for simultaneously detecting plural wavelengths is impossible. In more concrete terms, the wavelength sensitivity of a CCD photoreceiving apparatus which is employed as a detector in the citation is up to 1000 nm, and Raman scattered light can hardly be detected if the wavelength of excitation light is rendered in excess of 800 nm in response to a vital sample. Further, the wavelength sensitivity of the photomultiplier which is employed in the citation is also 300 to 1000 nm, and hence excitation light of a longer wavelength cannot be employed.

While excitation light in the range of 300 to 800 nm is employed as a result, the quantum efficiency of fluorescence is high in such a wavelength region, to reduce the signal-to-noise ratio of the Raman scattered light.

SUMMARY OF THE INVENTION

A first object of the present invention is to make a Raman scattered light measuring apparatus miniature and at a low cost.

A second object of the present invention is to simplify fluorescence avoidance and improve measuring sensitivity, for making a Raman scattered light measuring apparatus suitable for measuring a vital substance.

A Raman scattered light measuring apparatus according to the present invention comprises a bandpass filter (interference filter) including a vibration wavenumber which is specific to a target component in a sample to be measured in its transmission band or a cut filter which is combined to transmit the vibration wavenumber in its photoreceiving part.

In order to make it advantageous for measurement of a vital sample, a light source part comprises a near infrared semiconductor laser diode as a light source, and the photoreceiving part comprises a photodetector of Ge, InGaAs or PbS, a single-channel detector such as a photomultiplier having wavelength sensitivity in the range of 300 to 1700 nm, or a multi-channel detector such as a photodetector array of Ge, InGaAs or PbS as a detector for detecting Raman scattered light transmitted through the bandpass filter or the cut filter.

The near infrared semiconductor laser diode serving as the light source is preferably prepared from that having an oscillation wavelength of at least 800 nm in the range of 800 to 1600 nm, for example. GaAs/AlGaAs, InGaAs, InGaAsP or the like can be employed for such a near infrared semiconductor laser diode. When such a laser diode is employed, the cost can be reduced, the space can be saved and a compact Raman scattered light measuring apparatus can be implemented. While the laser diode may be instabilized in oscillation intensity, such instability of oscillation intensity can be corrected by detecting the light source intensity as a monitor and standardizing the detected intensity of Raman scattered light with the light source intensity.

When a near infrared region exceeding 800 nm is employed for an excitation wavelength, fluorescence is hardly generated from a vital substance, the background of Raman scattered light measurement is reduced and the signal-to-noise ratio of Raman scattered light measurement is improved to be suitable for analyzing a minor component.

This excitation wavelength region has smaller photon energy as compared with a visible region, whereby damage of the sample is reduced. Consequently, sample damage as well as an influence by fluorescence are small as compared with visible light excitation Raman spectroscopy, to be suitable for measurement of a vital substance.

If the sample is not a vital substance, a visible light source can be employed. In this case, the photoreceiving part can employ a silicon photodetector such as a CCD element or a silicon photodiode or a photomultiplier as a detector for detecting Raman scattered light which is transmitted through the bandpass filter or the cut filter.

According to the present invention, not a spectroscope but a bandpass filter or a cut filter is employed for selecting Raman scattered light and guiding the same to the detector. Raman scattered light of molecules to be measured has a specific vibration wavenumber by normal vibration of the molecules, and hence the bandpass filter may be so designed that the specific vibration wavenumber defines a central wavelength. In the bandpass filter, a light signal of a wavelength which is out of its transmission region is not incident upon the detector. The central wavelength of the transmission region is calculated from normal vibration analysis of the molecules to be measured, and the wavelength accuracy is high.

On the other hand, a combination of cut filters for cutting shorter and longer wavelength sides respectively can be employed for transmitting a vibration wavenumber which is specific to a sample component to be measured.

In case of employing the bandpass filter, a bandpass filter having a spectro-optic characteristic of a mathematical approximate function of the waveform of a target peak of a specific Raman scattering spectrum is preferable as an optical condition for efficiently detecting the Raman scattering spectrum. A peak waveform of a Raman scattering spectrum can be approximated with a mathematic function such as a Gaussian or Lorentz function, for example. In this case, transmission is made through a bandpass filter having a spectro-optic characteristic of the Gaussian or Lorentz function, whereby an integrated intensity of the target peak of the Raman scattering spectrum can be further correctly measured. If a target peak waveform of a Raman scattering spectrum can be approximated with another mathematic function, a bandpass filter having a spectro-optic characteristic of such a mathematic function is preferably employed.

The spectro-optic characteristics of the Gaussian and Lorentz functions can be expressed as follows respectively:

Gaussian function type:

$I = A \cdot \exp[-\{(x-xo)/(\alpha/2)\}^2]$

Lorentz function type:

$I = A[x/\{(xo^2 - x^2) + x^2\}]$ where I represents the intensity of transmitted light, x represents a wavelength, xo represents a central wavelength, $\alpha$ represents a half bandwidth, and A represents a constant.

FIGS. 2 and 3 show the relations between Raman scattering peak intensities and urogenous glucose concentrations measured by employing mixed solution samples prepared by dissolving glucose and acetone in urine while employing a laser beam of 1000 nm as excitation light through bandpass filters which were so designed that the central wavelengths of transmission regions were at a shift wavenumber of 1130 $cm^{-1}$ from the excitation light wavelength and the half bandwidth was 5 nm. Both of glucose and acetone concentrations were varied in the samples. FIG. 2 shows the results in case of employing a bandpass filter having unclarified spectrooptic characteristics, and FIG. 3 shows those in case of employing a bandpass filter (Gaussian filter) having Gaussian function type spectro-optic characteristics. Raman scattering at the shift wavenumber of 1130 $cm^{-1}$ derives from C—O stretching vibration of glucose, and its peak waveform can be approximated by both of Gaussian and Lorentz functions. From the results shown in FIG. 2, it is understood that the correlation coefficient R is so deteriorated that a Raman scattering spectrum of acetone is mixed into a target Raman scattering spectrum of glucose when a bandpass filter having spectro-optic characteristics of neither Gaussian nor Lorentz type is employed. On the other hand, it is understood from the results shown in FIG. 3 that a better correlation coefficient can be obtained through a bandpass filter having Gaussian spectro-optic characteristics so that a target spectrum can be accurately measured, regardless of the half bandwidth.

The correlation coefficient R is calculated as follows:

$$R = \frac{\sum\limits_{i=1}^{n} (xi - X)(yi - Y)}{\sqrt{\left[\sum\limits_{i=1}^{n} (xi - X)^2\right]\left[\sum\limits_{i=1}^{n} (yi - Y)^2\right]}}$$

where xi represents the concentration of each point of a measured sample, yi represents a measuring light intensity with respect to xi, X represents the mean concentration of each point of the measured sample, and Y represents the mean measuring light intensity.

FIG. 4 shows results of measurement of the same mixed solution samples as the above through a bandpass filter having Gaussian spectro-optic characteristics with a half bandwidth of 1 nm. As compared with the results shown in FIG. 3, it is understood that the correlation coefficients were so improved that it was possible to more accurately measure the target spectra due to the narrow half bandwidth, although the detected scattering light intensities (peak values) were substantially unchanged.

FIG. 5 shows results obtained by employing two bandpass filters having Gaussian spectro-optic characteristics with half bandwidths of 1 nm, which were overlapped with each other. As compared with the results shown in FIG. 4, it is understood that the correlation coefficients were further improved so that it was possible to more accurately measure target spectra, although detected scattered light intensities were reduced.

Due to employment of a bandpass filter, Rayleigh light removing filter is not necessary. The Rayleigh light removing filter is complicated to manufacture, and at a high cost. No employment of Rayleigh light removing filter contributes to cost reduction of the overall apparatus as well as to improvement in sensitivity with prevention of light quantity reduction.

Because no spectroscope was required, there is no such restriction that a condensing optical system must be matched with a spectroscope in selection, whereby the range of selection of the condensing optical system and optical components is widened. Further, it is possible to construct a bright optical system. Thus, the optical system is simplified and reduced in cost.

In order to increase Raman scattered light generation efficiency, the apparatus preferably comprises an integrating sphere type scattered light reinforcing holder for making multiple reflection of the excitation light as a holder for holding a sample cell. The sensitivity is improved when such an integrating sphere type scattered light reinforcing holder is employed. As the sample cell for making measurement with such an integrating sphere type scattered light reinforcing holder, a flow cell or a disposable cell is preferable.

Consequently, it is possible to simply measure a minor component in high accuracy by an apparatus which is at a low cost and can be miniaturized.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 6 is a block diagram expressing a first embodiment with concrete optical elements and components;

FIG. 7 is a block diagram expressing a second embodiment with concrete optical elements and components;

FIGS. 9A, 9B and 9C are a front elevational view, a plan view and a perspective view showing an exemplary sample cell;

DESCRIPTION OF THE PREFERRED EMBODIMENTS

Figure 1:
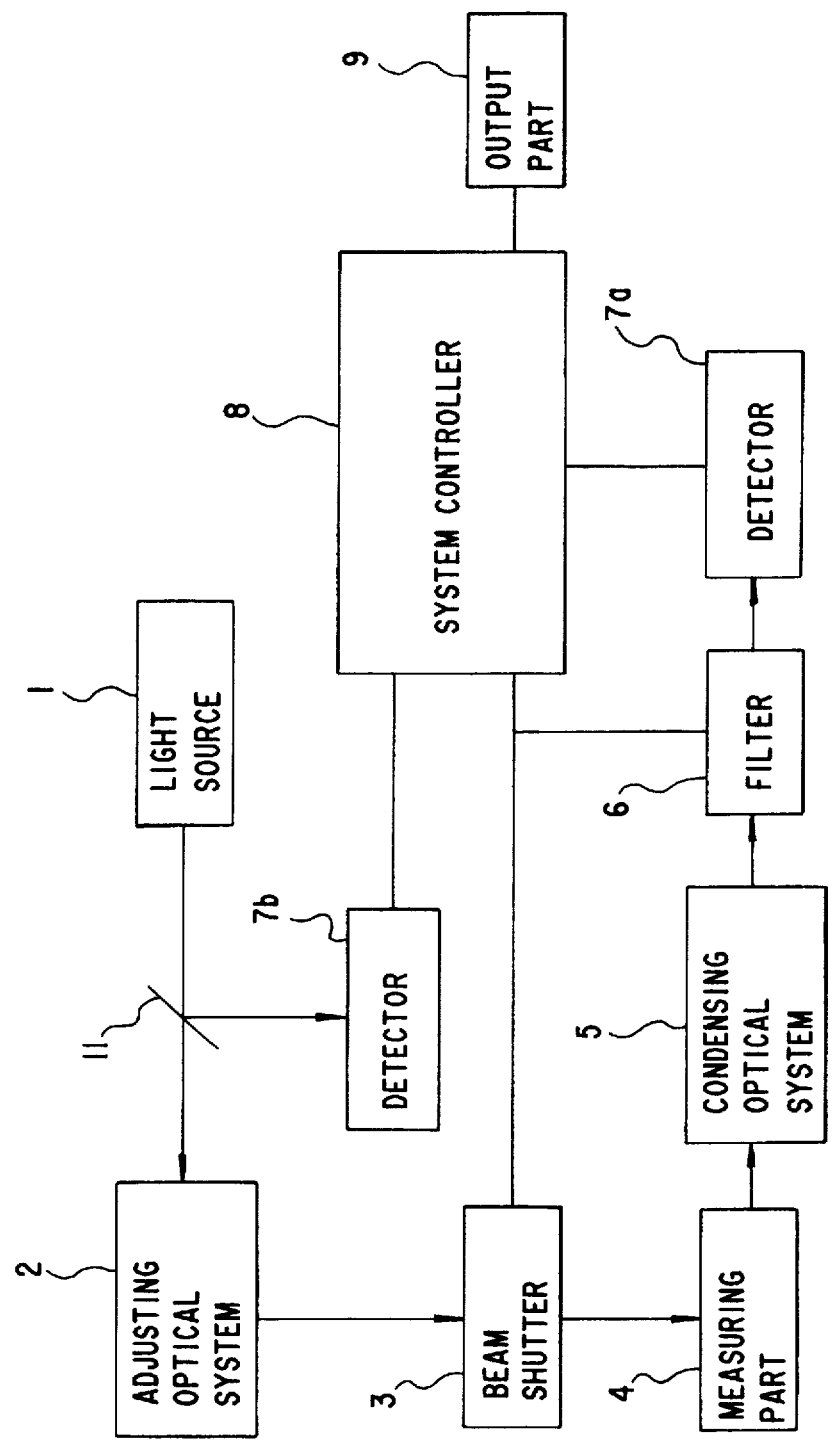
FIG. 1 is a block diagram schematically showing an apparatus according to the present invention.
Figure 2:
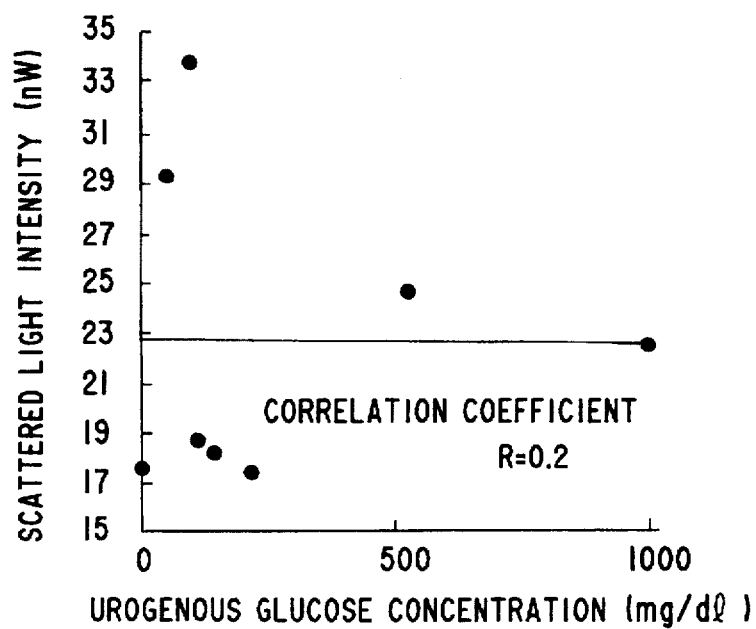
FIG. 2 illustrates a graph showing the relations between Raman scattering peak intensities and urogenous glucose concentrations in mixed solution samples prepared by dissolving glucose and acetone in urine measured through a bandpass filter having a half bandwidth of 5 nm and unclarified spectro-optic characteristics.
Figure 3:
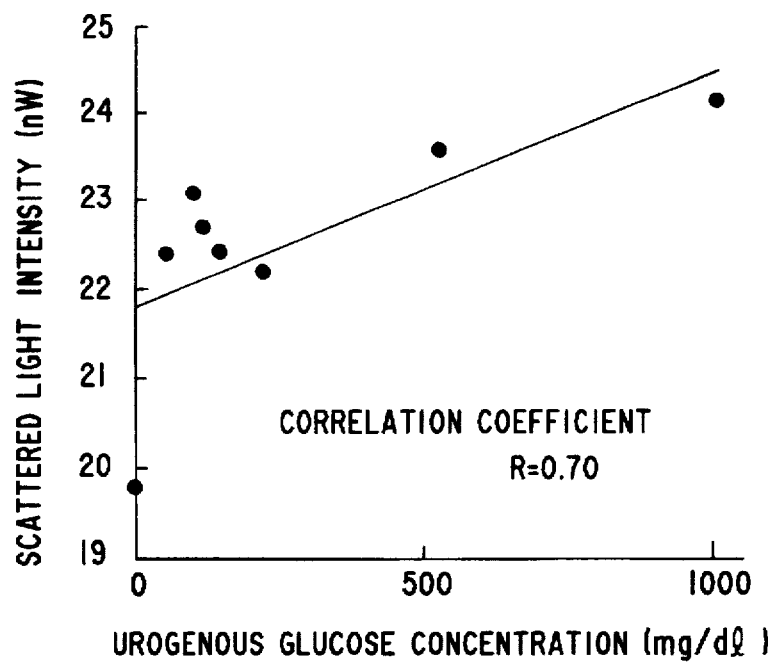
FIG. 3 illustrates a graph showing the relations between Raman scattering peak intensities and urogenous glucose concentrations in mixed solution samples prepared by dissolving glucose and acetone in urine measured through a bandpass filter having a half bandwidth of 5 nm and Gaussian function type spectro-optic characteristics.
Figure 4:
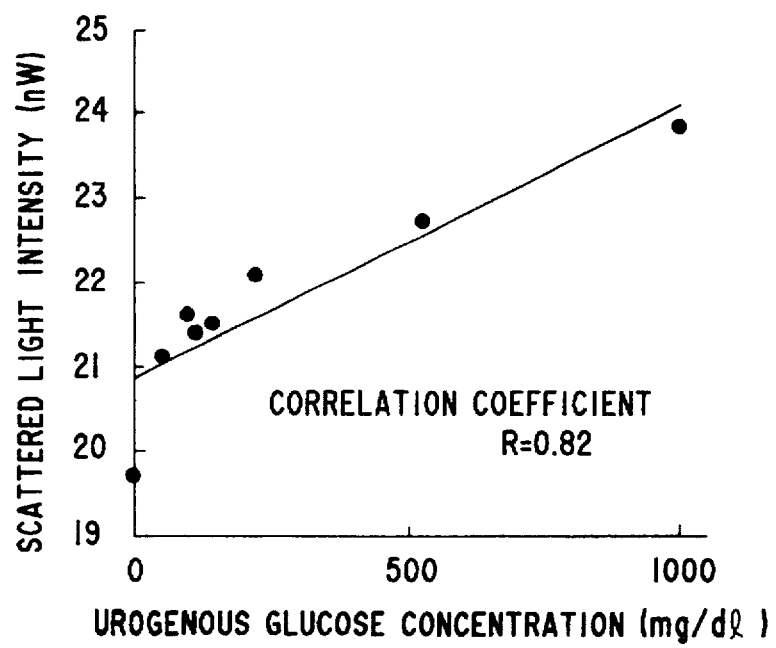
FIG. 4 illustrates a graph showing the relations between Raman scattering peak intensities and urogenous glucose concentrations in mixed solution samples prepared by dissolving glucose and acetone in urine measured through a bandpass filter having a half bandwidth of 1 nm and Gaussian function type spectro-optic characteristics.
Figure 5:
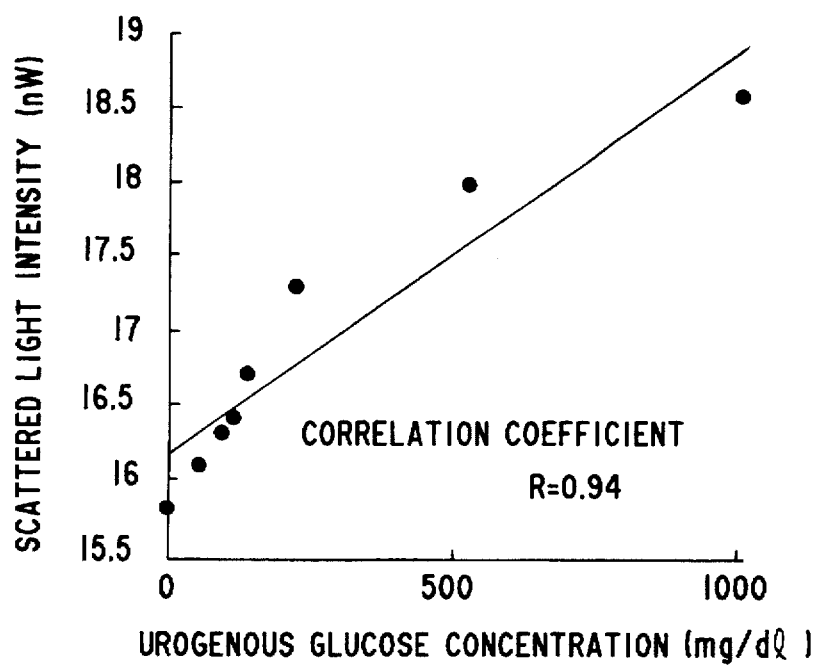
FIG. 5 illustrates a graph showing the relations between Raman scattering peak intensities and urogenous glucose concentrations in mixed solution samples prepared by dissolving glucose and acetone in urine measured through two bandpass filters having half bandwidths of 5 nm and Gaussian function type spectro-optic characteristics.
Figure 8B:
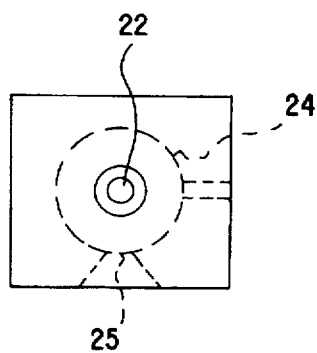
FIGS. 8A, 8B, 8C and 8D are a front elevational view, a plan view, a right side elevational view and an exploded perspective view showing an integrating sphere type scattered light reinforcing holder serving as an exemplary sample cell holder respectively.
Figure 8D:
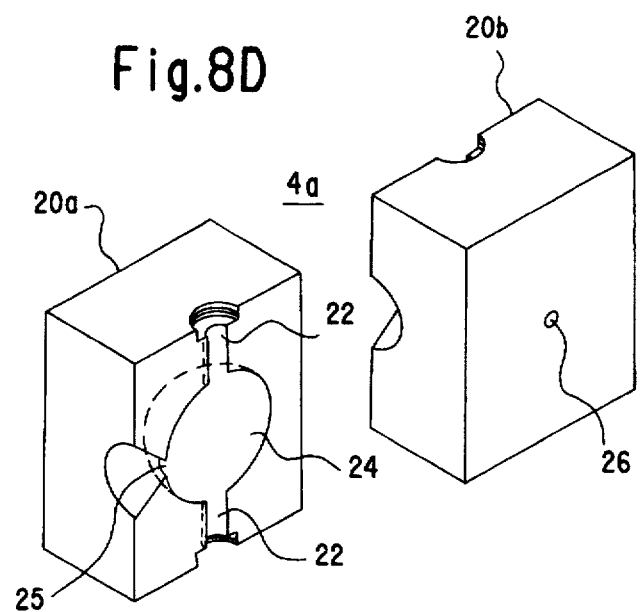
Figure 8A:
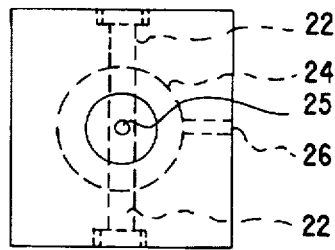
Figure 8C:
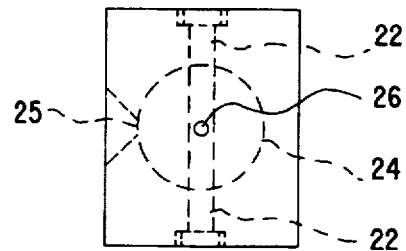

FIG. 1 schematically illustrates an apparatus according to the present invention.

Numeral 1 denotes an excitation light source and its controller, numeral 2 denotes an excitation light adjusting optical system for adjusting excitation light from the light source for irradiating a sample cell with the excitation light, numeral 3 denotes a beam shutter for intermittently controlling the excitation light applied to the sample cell and its controller, numeral 4 denotes a measuring part including the sample cell, numeral 5 denotes a scattered light condensing optical system for condensing scattered light generated from a sample irradiated with the excitation light and condensing and guiding the scattered light to a detector, numeral 6 denotes a bandpass filter or a combined cut filter for taking out Raman scattered light from the scattered light from the sample, and numeral 7a denotes the detector and its controller. Numeral 8 denotes a system controller for controlling an operation of the beam shutter 3, an operation of switching the filter 6 and selecting a wavelength and the like while data-processing a detection signal by the detector 7a, and numeral 9 denotes a data output part for outputting the data processed by the system controller 8.

In order to correct the light source intensity, a beam splitter 11 may be arranged on an optical path of the excitation light from the light source 1 for taking out part of the excitation light, detecting its intensity by a detector 7b which is different from that on the sample side, and guiding its output to the system controller 8.

FIG. 6 is a block diagram expressing the structure of FIG. 1 with concrete optical elements and components and showing an embodiment employing a near infrared light source.

For example, an InGaAs laser diode by SDL, U.S.A., having an oscillation wavelength of 1000 nm is provided as an excitation light source 1a of an excitation light source and its controller 1. Numeral 1b denotes a laser driver, which is its controller, comprising a Peltier element as cooling means. In order to converge excitation light from the excitation light source 1a on a sample in a sample cell of a measuring part 4, condenser lenses 2a and 2b and a mirror 2c which is arranged on an optical path therebetween are provided as an excitation light adjusting optical system 2.

An electronic shutter 3a is arranged on an optical path between the condenser lens 2a and the mirror 2c, as a beam shutter of a beam shutter and controller 3. Numeral 3b denotes a controller of the electronic shutter 3a.

An excitation side bandpass filter 10 is arranged on an optical path between the mirror 2c and the condenser lens 2a, in order to irradiate the sample with only an excitation light component of a desired wavelength in the excitation light from the excitation light source 1a.

The measuring part 4 comprises a sample cell holder 4a and a flow cell type sample cell 4b concretely described later with reference to FIGS. 8A to 8D and 9A to 9C, so that the sample flows through the sample cell 4b to be irradiated with the excitation light therein.

A detector and controller 7a comprises a photodetector of Ge, InAs or PbS, or a photomultiplier having wavelength sensitivity in the range of 300 to 1700 nm serving as the detector, its controller, and an A-D converter for converting a detection signal of the detector to a digital signal. The photomultiplier may be prepared from R5509-41 or -71 (product by Hamamatsu Photonics Co., Ltd.).

In order to condense scattered light generated from the sample in the sample cell 4b and converge the same on the detector 7a, convergent lenses 5a and 5b are provided on an optical path between the sample cell 4b and the detector 7a as a scattered light condensing optical system 5. A bandpass filter 6 which is so designed as to transmit Raman scattered light of target molecules from the scattered light generated from the sample is arranged on an optical path between the convergent lenses 5a and 5b.

A plurality of filters 6a having different transmission wavelengths are arranged on the circumference of a discoidal support plate 6b in the bandpass filter 6, and the support plate 6b is rotated by a stepping motor 6c for positioning a desired filter 6a on the optical path of the scattered light. Numeral 6d denotes a controller for the stepping motor 6c.

A personal computer is employed as a system controller 8 for controlling the laser driver 1b, the controller 3b for the electronic shutter 3a and the controller 6d for the stepping motor 6c, inputting an output signal by the detector 7a and performing data processing such as qualification and determination of a target component. The result of the data processing by the personal computer 8 is outputted on a printer serving as a data output part 9.

FIG. 7 shows a structural embodiment comprising a correction optical system for correcting fluctuation of a light source intensity.

An excitation side bandpass filter 10 is arranged between an electronic shutter 3a and a mirror 2c, and a beam splitter 11 is arranged between the excitation side bandpass filter 10 and the mirror 2c, in order to take out part of excitation light from a light source. The excitation light taken out by the beam splitter 11 is incident upon and detected by a detector 7b through a neutral density filter 13 for adjusting its intensity. The detector 7b comprises an A-D converter for converting its detection signal to a digital signal, so that the digitized detection signal is inputted in a personal computer 8 as a signal for correcting fluctuation of the excitation light intensity and the detection signal by the detector 7a is corrected.

When measurement is made in a visible region, a light source and a detector for visible application may be employed.

FIGS. 8A, 8B, 8C and 8D are a front elevational view, a plan view, a right side elevational view and an exploded perspective view showing an integrating sphere type scattered light reinforcing holder serving as the sample cell holder 4a in the measuring part 4 respectively.

The sample cell holder 4a consists of two members 20a and 20b, and comprises cell holding parts 22 on both ends, an integrating sphere part 24 which is held between and connected with the cell holding parts 22, an incidence hole 25 for irradiating a cell which is held by the integrating sphere part 24 with excitation light, and an outgoing hole 26 for taking out scattered light generated from a sample in the cell to the exterior.

While the excitation light incident direction and the scattered light taking out direction are at 90 degrees in the embodiment shown in FIGS. 8A to 8D, these directions may alternatively be at 180 degrees, i.e., the incidence hole 25 and the outgoing hole 26 may be a common single hole.

FIGS. 9A, 9B and 9C are a front elevational view, a plan view and a perspective view showing a flow cell 4b which is suitably mounted on the cell holder 4a shown in FIGS. 8A to 8D. A part of the flow cell 4b feeding the sample is made of quartz, and this flow cell 4b comprises a spherical part 30 which is attached to the integrating sphere part 24 of the cell holder 4a, and cylindrical inlet/outlet parts 32 which extend on both sides thereof to be attached to the cell holding parts 22. The inlet/outlet parts 32 are provided with flanges 34 to be fixed to the cell holder 4a.

Figure 10A:
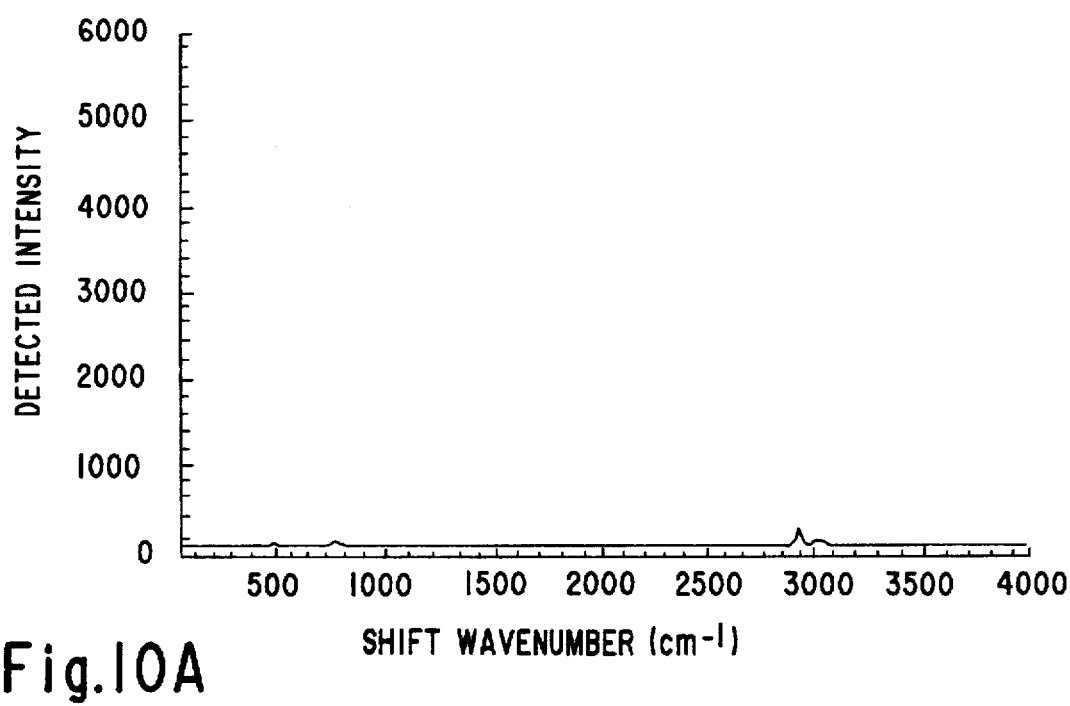
FIGS. 10A and 10B illustrate results of Raman scattering spectra measured through FT-Raman spectrophotometers provided with no cell holder and with the integrating type cell holder shown in FIG. 8 respectively for indicating the function of the cell holder in the embodiment.
Figure 10B:
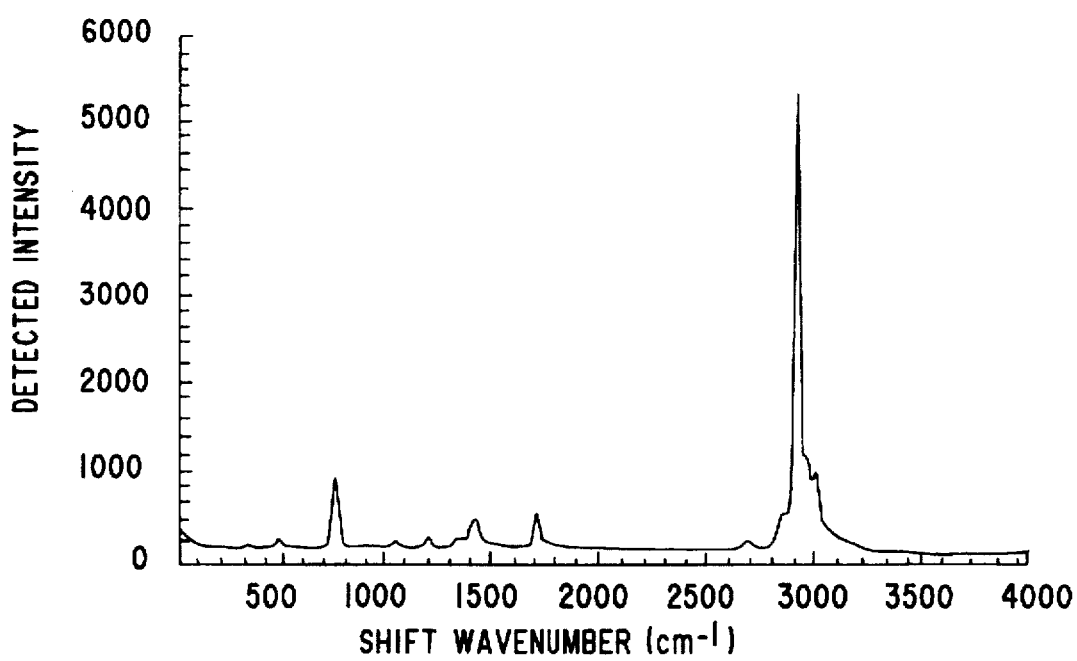
Figure 11A:
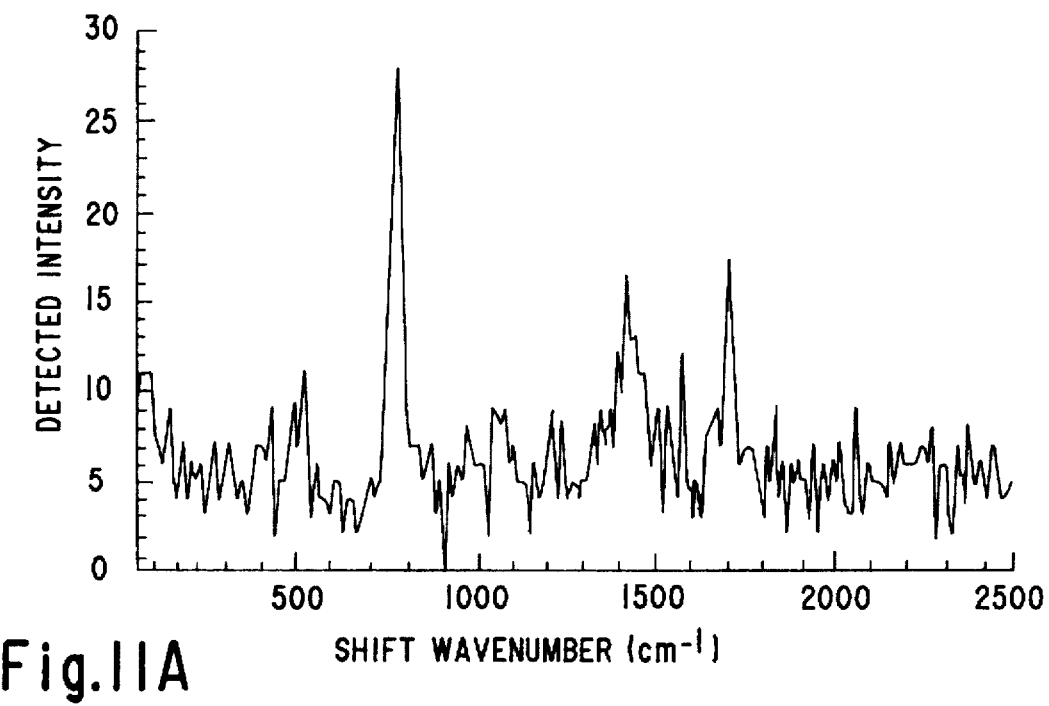
FIGS. 11A and 11B illustrate the same results as FIGS. 10A and 10B with increased gains.
Figure 11B:
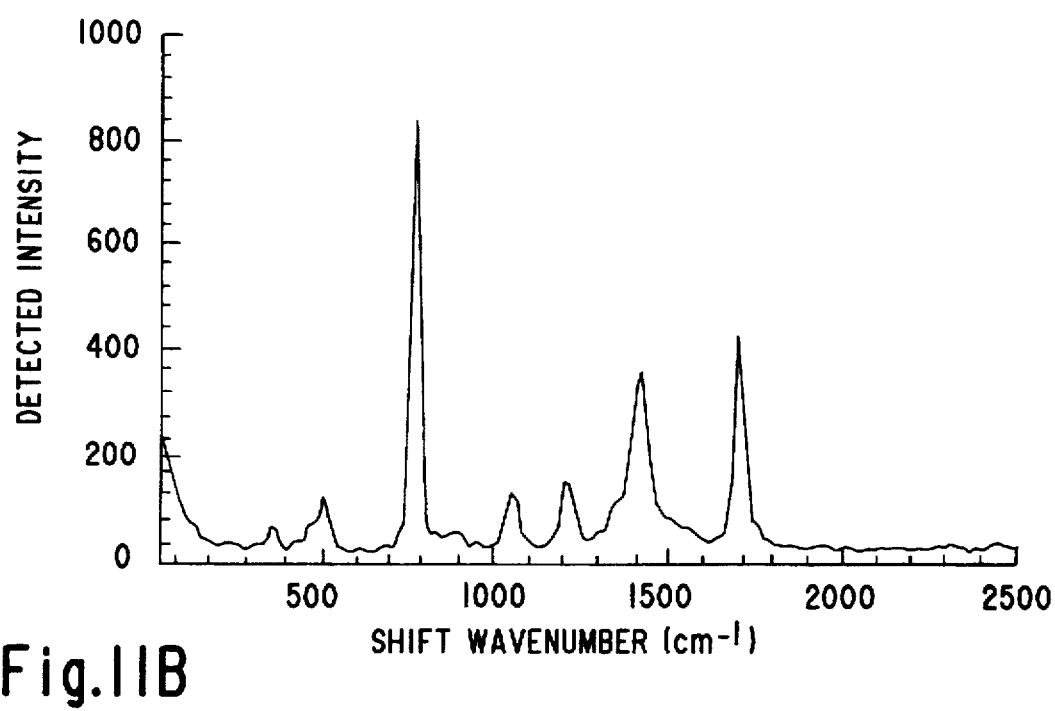

FIGS. 10A, 10B, 11A and 11B illustrate results of Raman scattering spectra of 99% acetone measured through conventional Raman scattering measuring apparatuses (FT-Raman spectrophotometers) comprising Fourier transform spectroscopes respectively. InGaAs laser diodes (by SDL, U.S.A.) of 1000 nm in oscillation wavelength and 50 mW in output were employed as light sources. FIGS. 10A and 11A illustrate the case of employing no cell holder, and FIGS. 10B and 11B illustrate the case of employing the integrating sphere type cell holder 4a shown in FIGS. 8A to 8D respectively. The axes of ordinates show detected intensities, and the axes of abscissas show shift wavenumbers from excitation wavelengths.

FIGS. 10A and 10B show the results compared on the same scale of the detected intensities on the axes of ordinates, and FIGS. 11A and 11B show the same results as those in FIGS. 10A and 10B while increasing the gains of FIG. 11A in the range of shift wavenumbers of 0 to 2500 cm$^{-1}$ to attain substantially equal peak heights. From these results, it is understood that Raman scattered light was reinforced to about 30 times by employing the integrating sphere type cell holder shown in FIGS. 8A to 8D. Further, the S-N ratios were also improved as clearly understood from the comparison results of FIGS. 11A and 11b.

Figure 12A:
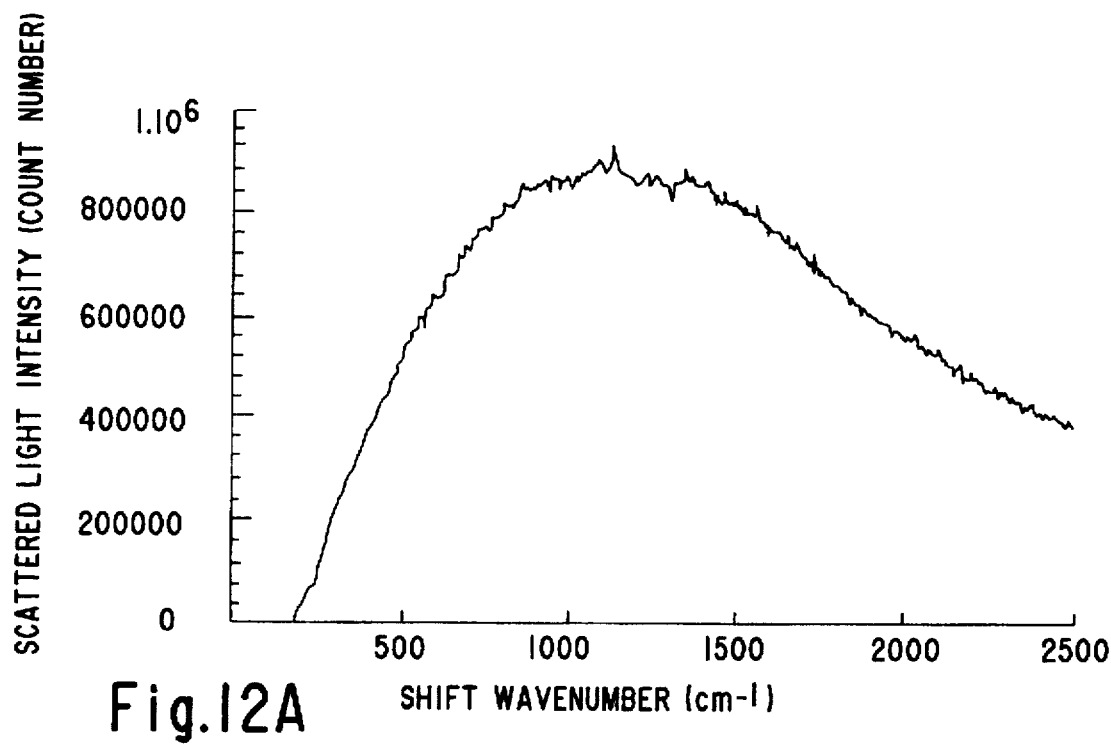
FIGS. 12A and 12B illustrate results of Raman scattering spectra measured through a Raman spectrophotometer with excitation light of a visible region and through an FT-Raman spectrophotometer with excitation light of a near infrared region respectively for indicating influences by excitation light wavelengths.
Figure 12B:
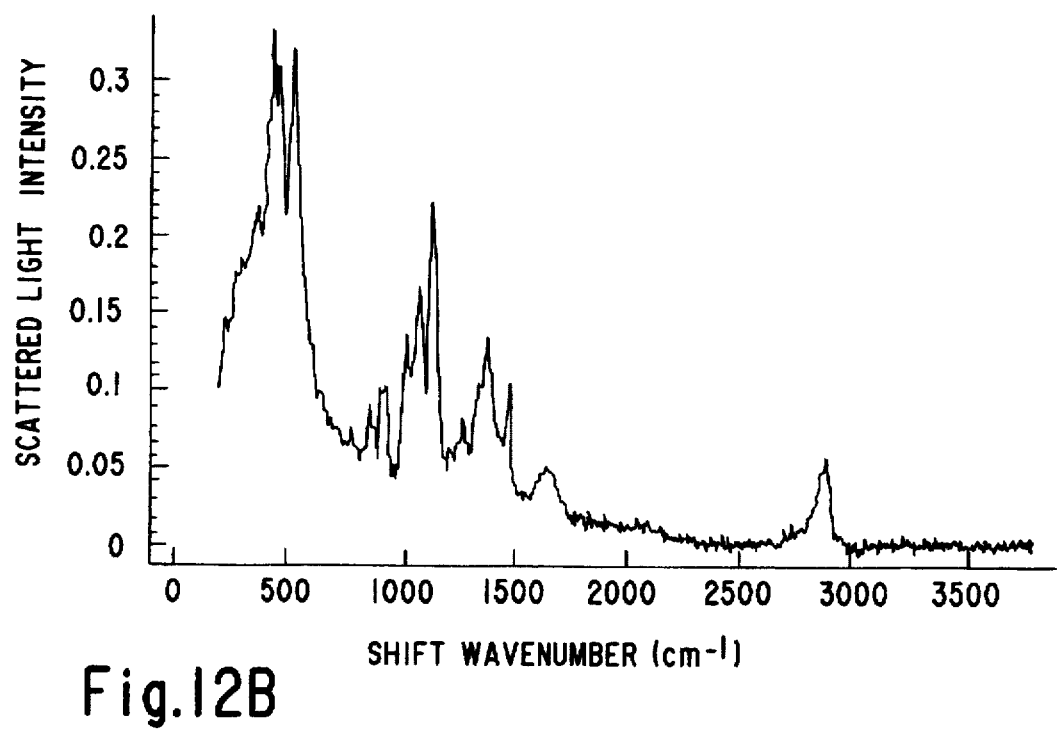

FIGS. 12A and 12B illustrate results of Raman scattering measurement through wavelengths of excitation light. Samples were prepared by adding glucose into urine to be 2M. FIG. 12A shows a spectrum measured by employing an argon ion laser beam of 514.5 nm of a visible region as excitation light through a Raman spectrophotometer having a CCD detection element as a detector. In this case, an influence by fluorescence was so strong that it was difficult to determine peaks of Raman scattering by glucose. Thus, determination of glucose by Raman scattering was difficult.

On the other hand, FIG. 12B shows a spectrum measured by employing a laser beam of 1000 nm in a near infrared region by a laser diode as excitation light through an FT-Raman spectrophotometer comprising a near infrared detector. In this case, an influence by fluorescence was small and Raman scattering peaks clearly appeared. For example, the peak appearing at 1130 cm$^{-1}$ is Raman scattering based on C-O stretching vibration of glucose, and glucose can be determined through this peak.

Figure 13A:
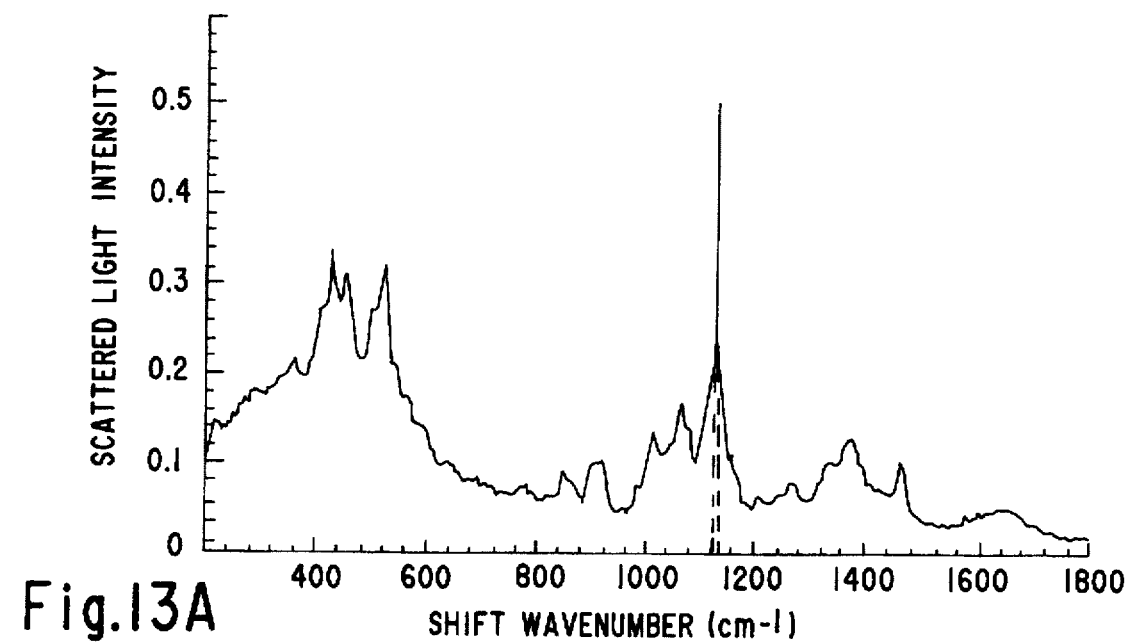
FIG. 13A illustrates a Raman scattering spectrum (solid line) of an urogenous glucose sample measured through an FT-Raman spectrophotometer and transmission wavelength characteristics (broken lines) of a bandpass filter which was so designed that the central wavelength of its transmission region was at a shift wavenumber of 1130 $cm^{-1}$ from an excitation light wavelength and the half bandwidth was 1 nm.

A solid line shown in FIG. 13A illustrates a Raman spectrum of a sample containing 2M of glucose in urine measured by employing a laser beam of 1000 nm through an FT-Raman spectrophotometer, similarly to FIG. 12B. Broken lines in FIG. 13A show transmission wavelength characteristics of a holographic bandpass filter having Gaussian function type spectro-optic characteristics, which was so designed that the central wavelength of its transmission region was at a shift wavenumber of 1130 cm$^{-1}$ from an excitation light wavelength, the half bandwidth was 1 nm and the transmittance was 98%.

In the following measurement examples, all bandpass filters were prepared from those having Gaussian spectro-optic characteristics (products by Barr Associates, Inc., U.S.A.).

Figure 13B:
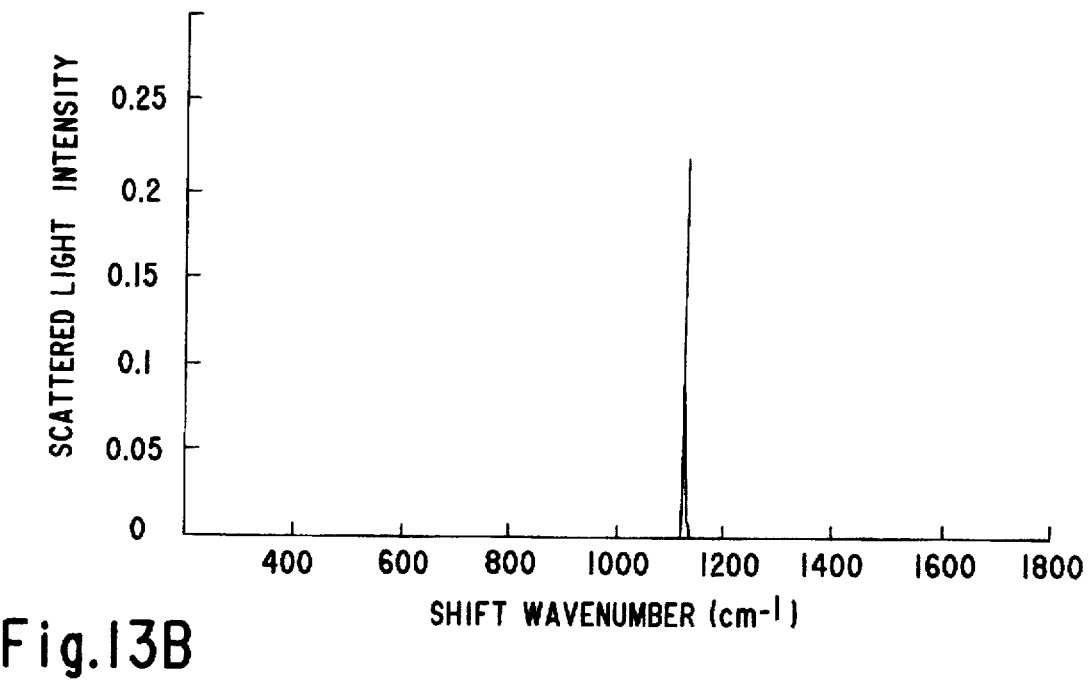
FIG. 13B illustrates a result of measurement of the urogenous glucose sample through the measuring apparatus of the embodiment shown in FIG. 6 comprising the bandpass filter having the transmission wavelength characteristics shown by the broken lines in FIG. 13A respectively.

FIG. 13B shows a result obtained by measuring the urogenous glucose sample through the measuring apparatus shown in FIG. 6 by employing a laser beam of 1000 nm while using a bandpass filter having the transmission wavelength characteristics shown by the broken lines in FIG. 13A. Only a peak at a shift wavenumber of 1130 cm$^{-1}$ from an excitation light wavelength was detected. Quantitative measurement of glucose in a sample can be made through this peak.

Figure 14:
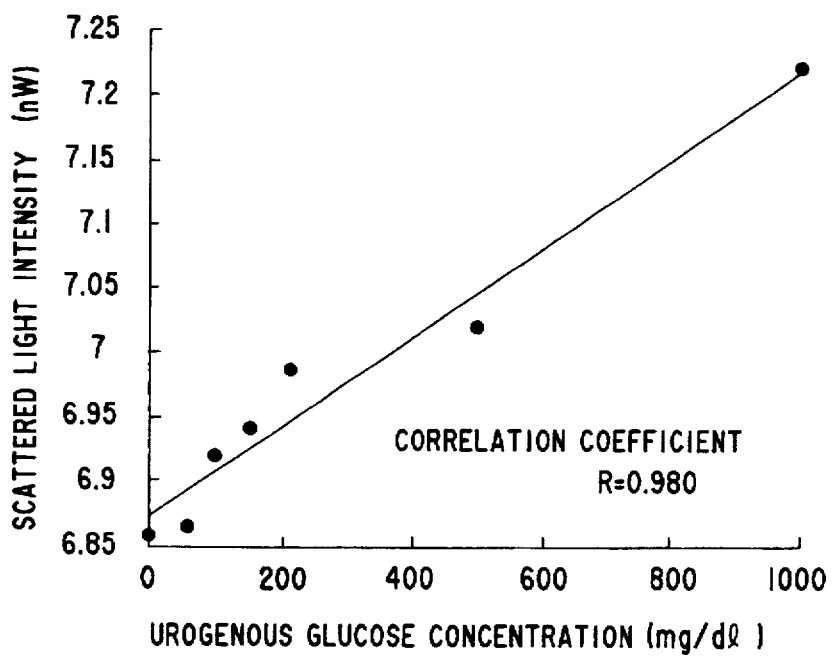
FIG. 14 illustrates a graph showing the relations between Raman peak intensities at a shift wavenumber of 1130 $cm^{-1}$ and urogenous glucose concentrations by the apparatus of the embodiment which was so designed that the half bandwidth was 1 nm.

FIG. 14 shows the relations between urogenous glucose concentrations and Raman scattering peak intensities on the basis of the Raman scattering peak intensities at a shift wavenumber of 1130 cm$^{-1}$ in case of employing a bandpass filter having a half bandwidth of 1 nm through the same measuring apparatus as that employed for obtaining the peak shown in FIG. 13B. The urogenous glucose concentrations were measured through a sugar meter (GT-1620 by Kyoto Dai-ichi Kagaku Co., Ltd.).

The correlation coefficient R of a straight line shown in FIG. 14 was 0.980.

Figure 15A:
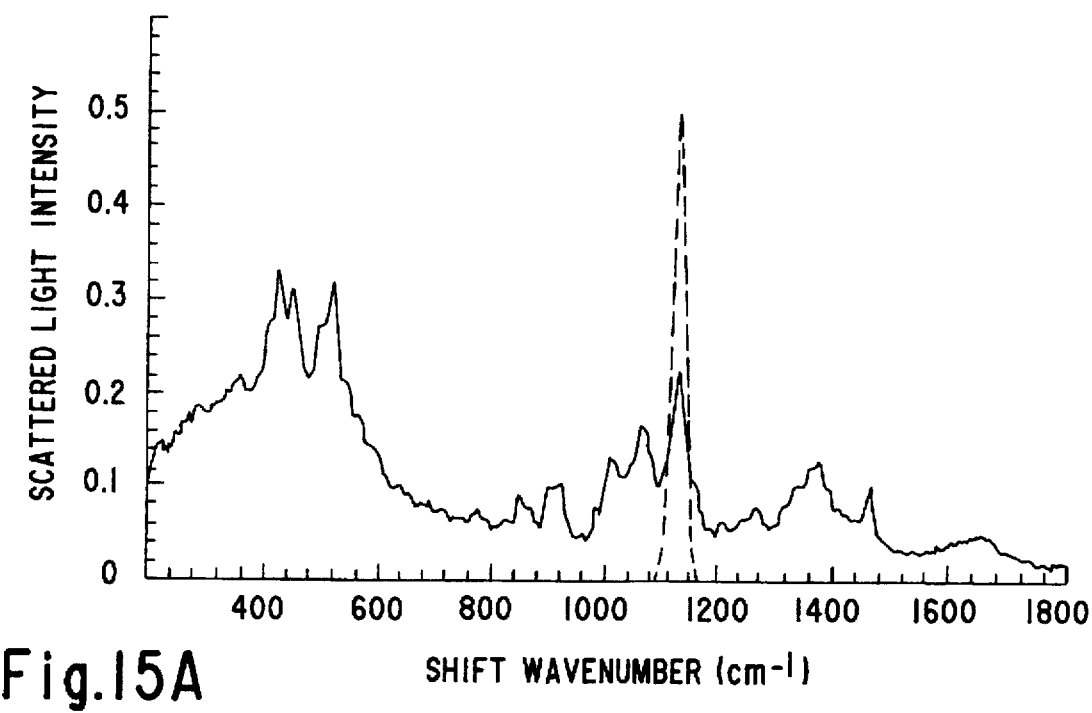
FIG. 15A illustrates a Raman scattering spectrum (solid line) of an urogenous glucose sample measured through an FT-Raman spectrophotometer and transmission wavelength characteristics (broken lines) of a bandpass filter which was so designed that the central wavelength of its transmission region was at a shift wavenumber of 1130 $cm^{-1}$ from an excitation light wavelength and the half bandwidth was 5 nm.

FIG. 15A shows a Raman spectrum of a sample containing 2M of glucose in urine measured by employing a laser beam of 1000 nm through an FT-Raman spectrophotometer, similarly to FIG. 12B. Broken lines in FIG. 15A show transmission wavelength characteristics of a holographic bandpass filter which was so designed that the central wavelength of its transmission region was at a shift wavenumber of 1130 cm$^{-1}$ from an excitation light wavelength, the half bandwidth was 5 nm and the transmittance was 98%.

Figure 15B:
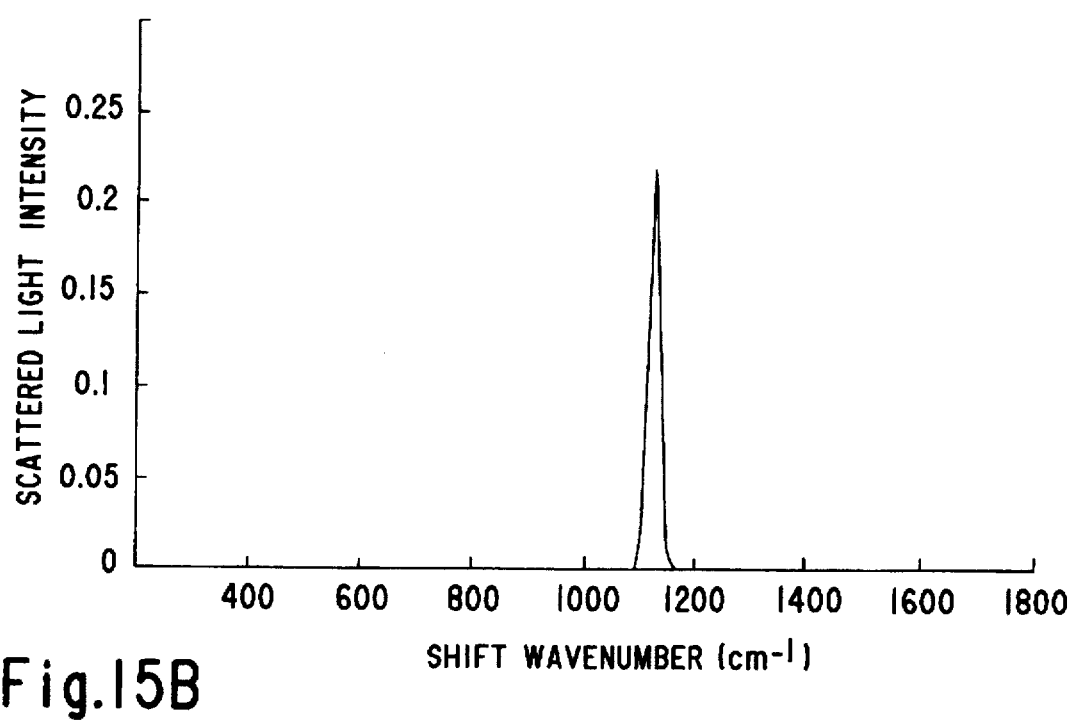
FIG. 15B illustrates a result of measurement of the urogenous glucose sample through the measuring apparatus of the embodiment shown in FIG. 6 comprising the bandpass filter having the transmission wavelength characteristics shown by the broken lines in FIG. 15A respectively.

FIG. 15B shows a result obtained by measuring the urogenous glucose sample through the measuring apparatus shown in FIG. 6 by employing a laser beam of 1000 nm while using a bandpass filter having the transmission wavelength characteristics shown by the broken lines in FIG. 15A. Only a peak at a shift wavenumber of 1130 cm$^{-1}$ from an excitation light wavelength was detected. Quantitative measurement of glucose in a sample can be made through this peak.

Figure 16:
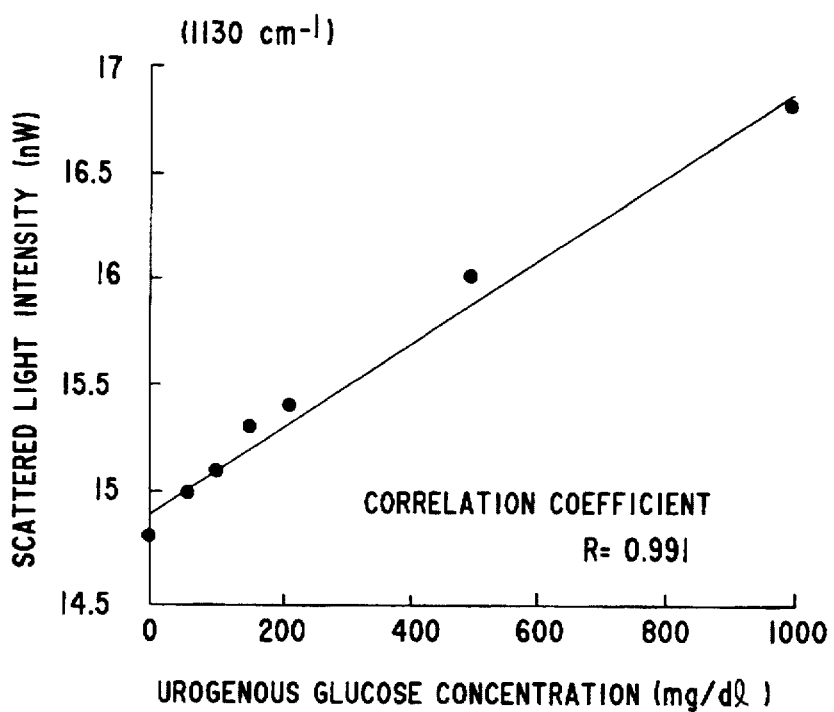
FIG. 16 illustrates a graph showing the relations between Raman peak intensities at a shift wavenumber of 1130 $cm^{-1}$ and urogenous glucose concentrations by the apparatus of the embodiment comprising the bandpass filter which was so designed that the half bandwidth was 5 nm.

FIG. 16 shows the relations between urogenous glucose concentrations and Raman scattering peak intensities measured on the basis of the Raman scattering peak intensities at a shift wavenumber of 1130 cm$^{-1}$ in case of employing a bandpass filter having a half bandwidth of 5 nm through the same measuring apparatus as that employed for obtaining the peak shown in FIG. 15B. The correlation coefficient R of a straight line shown in FIG. 16 was 0.991.

Figure 17A:
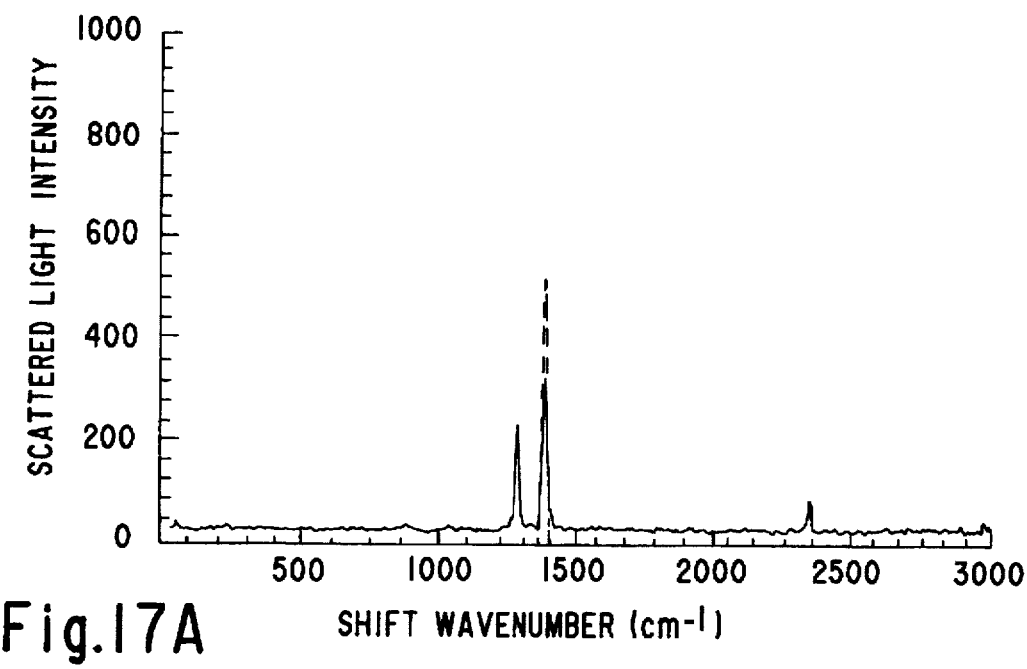
FIG. 17A illustrates a Raman spectrum (solid line) of $CO_2$ gas measured through a Raman spectrophotometer and transmission wavelength characteristics (broken lines) of a bandpass filter which was so designed that the central wavelength of its transmission region was at a shift wavenumber of 1386 $cm^{-1}$ from an excitation light wavelength and the half bandwidth was 1 nm.

A solid line shown in FIG. 17A illustrates a Raman spectrum of $CO_2$ gas measured by employing an argon ion laser beam of 514.5 nm of a visible region as excitation light through a Raman spectrophotometer having a CCD detection element as a detector. Broken lines in FIG. 17A show transmission wavelength characteristics of a bandpass filter which was so designed that the central wavelength of its transmission region was at a shift wavenumber of 1386 cm$^{-1}$ from an excitation light wavelength and the half bandwidth was 1 nm.

Figure 17B:
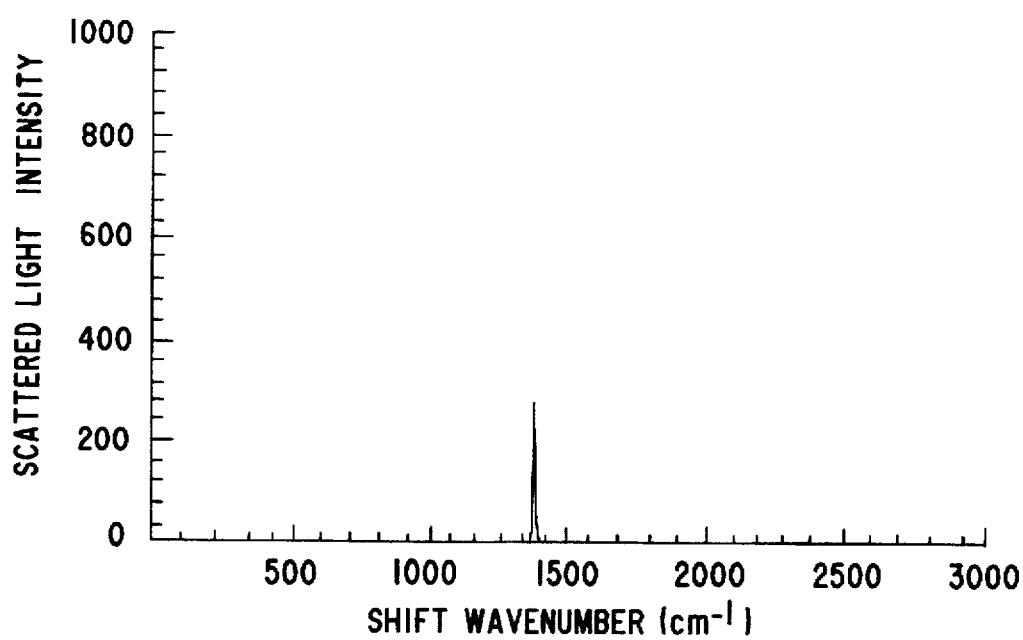
FIG. 17B illustrates a result of measurement of the $CO_2$ gas through the measuring apparatus of the embodiment shown in FIG. 6 comprising the bandpass filter having the transmission wavelength characteristics shown by the broken lines in FIG. 17A respectively.

FIG. 17B shows a result of measurement of $CO_2$ gas through the measuring apparatus shown in FIG. 6 by employing an argon ion laser beam of 514.5 nm while using a bandpass filter having the transmission wavelength characteristics shown by the broken lines in FIG. 17A. Only a peak at a shift wavenumber of 1386 cm$^{-1}$ from an excitation light wavelength was detected. Quantitative measurement of $CO_2$ in a sample can be made through this peak.

Figure 18A:
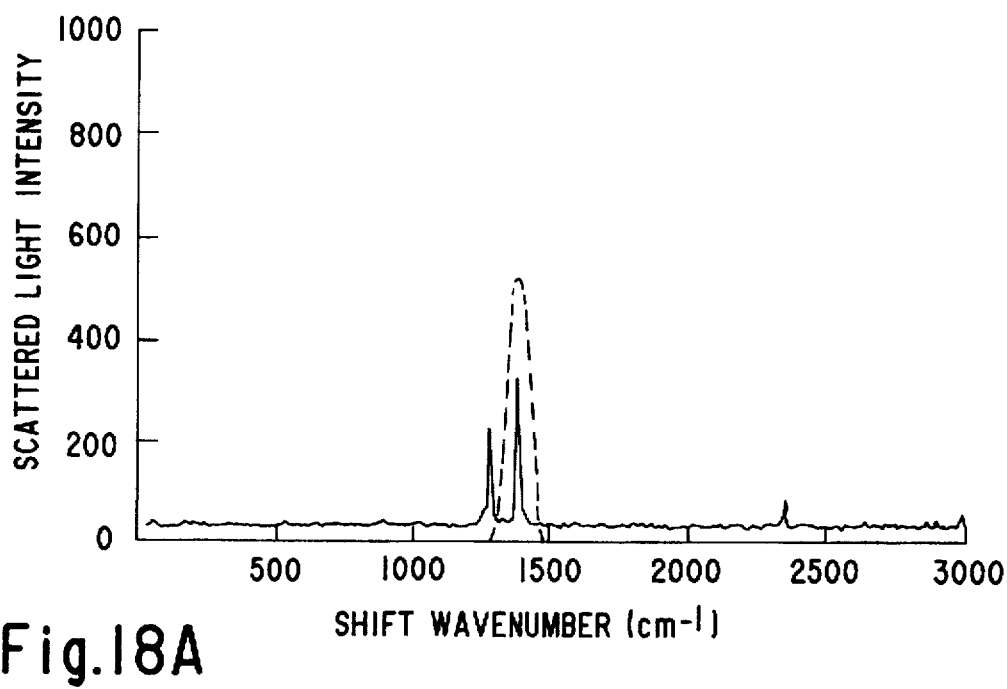
FIG. 18A illustrates a Raman spectrum (solid line) of $CO_2$ gas measured through a Raman spectrophotometer and transmission wavelength characteristics (broken lines) of a bandpass filter which was so designed that the central wavelength of its transmission region was at a shift wavenumber of 1386 $cm^{-1}$ from an excitation light wavelength and the half bandwidth was 5 nm.

A solid line shown in FIG. 18A illustrates a Raman spectrum of $CO_2$ gas measured by employing an argon ion laser beam of 514.5 nm of a visible region as excitation light through a Raman spectrophotometer having a CCD detection element as a detector. Broken lines in FIG. 18A show transmission wavelength characteristics of a bandpass filter which was so designed that the central wavelength of its transmission region was at a shift wavenumber of 1386 cm$^{-1}$ from an excitation light wavelength and the half bandwidth was 5 nm.

Figure 18B:
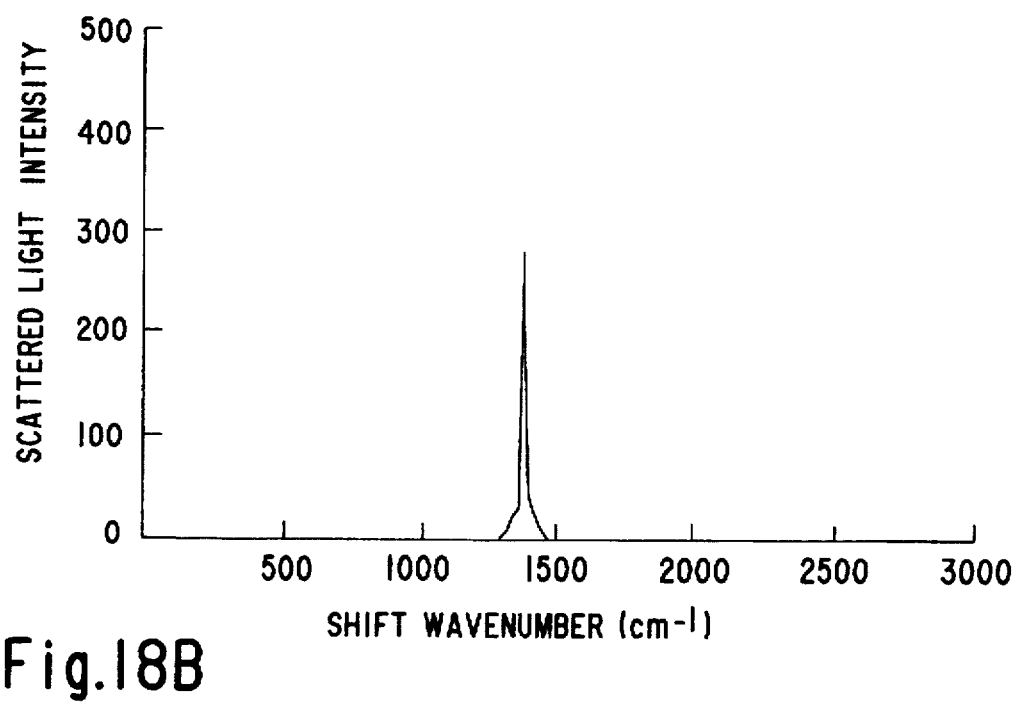
FIG. 18B illustrates a result of measurement of the $CO_2$ gas through the measuring apparatus of the embodiment shown in FIG. 6 comprising the bandpass filter having the transmission wavelength characteristics shown by the broken lines in FIG. 18A respectively.

FIG. 18B shows a result of measurement of $CO_2$ gas through the measuring apparatus of the embodiment shown in FIG. 6 by employing an argon ion laser beam of 514.5 nm while using a bandpass filter having the transmission wavelength characteristics shown by the broken lines in FIG. 18A. While scattered light around a peak at a shift wavenumber of 1386 cm$^{-1}$ from an excitation light wavelength was detected, quantitative measurement of $CO_2$ in a sample can be made through this peak.

Figure 19:
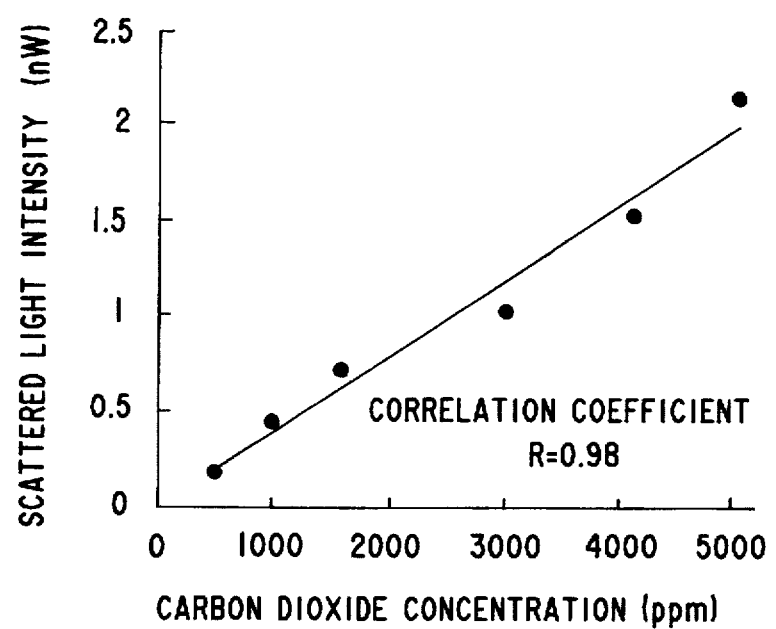
FIG. 19 illustrates a table and a graph showing the relations between Raman peak intensities at a shift wavenumber of 1386 $cm^{-1}$ and $CO_2$ concentrations in gas by the apparatus of the embodiment comprising a bandpass filter which was so designed that the half bandwidth was 1 nm.

FIG. 19 shows the relations between $CO_2$ in gas and Raman scattering peak intensities on the basis of the peak intensities at a shift wavenumber of 1386 cm$^{-1}$ measured by the same measuring apparatus as that obtaining the peak of FIG. 18B. The correlation coefficient R of a straight line shown in FIG. 19 was 0.98.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A Raman scattered light measuring apparatus for irradiating a sample in a sample part to detect Raman scattered light from said sample and thereby measure a target component in said sample, said apparatus comprising:

a near infrared semiconductor laser diode having a wavelength of at least 800 nm for irradiating said sample with excitation light;

a photo receiving part consisting of a filter which passes light having a specific vibration wave number of said target component;

a first detector, comprising a photodetector consisting of Ge, InGaAs or PbS, for detecting said Raman scattered light being transmitted through said filter.

2. A Raman scattered light measuring apparatus for irradiating a sample in a sample part to detect Raman scattered light from said sample and thereby measure a target component in said sample, said apparatus comprising:

a near infrared semiconductor laser diode having a wavelength of at least 800 nm for irradiating said sample with excitation light;

a photo receiving part consisting of a filter which passes light having a specific vibration wave number of said target component;

a first detector, comprising a photomultiplier having sensitivity in a near infrared region, for detecting said Raman scattered light being transmitted through said filter.

3. The Raman scattered light measuring apparatus in accordance with claim 1 or 2, further comprising a beam splitter being provided on an optical path between said near infrared semiconductor laser diode and said sample part for taking out part of said excitation light and a second detector for detecting said taken-out excitation light, an output signal of said first detector being corrected as a function of the intensity of said excitation light.

4. The Raman scattered light measuring apparatus in accordance with claims 1 or 2, wherein said filter is a bandpass filter which has spectro-optic characteristics of a mathematical approximate function of the wave form of a target peak of a Raman scattering spectrum or a function being close thereto.

5. The Raman scattered light measuring apparatus in accordance with claim 4, wherein said bandpass filter has spectro-optic characteristics of a Gaussian or Lorentz function.

6. The Raman scattered light measuring apparatus in accordance with claim 4, wherein said bandpass filter comprises two bandpass filters overlapped with each other.

7. The Raman scattered light measuring apparatus in accordance with claim 1 or 2, wherein said sample part comprises an integrating sphere type scattered light reinforcing holder for holding a sample cell.

* * * * *